(12) United States Patent
Chiang et al.

(10) Patent No.: US 11,079,374 B2
(45) Date of Patent: Aug. 3, 2021

(54) METHODS AND KITS FOR EXOSOME ISOLATION AND QUANTIFICATION

(71) Applicants: Dapi Meng Lin Chiang, Taipei (TW); Michael W. Pfaffl, Freising (DE); Biovesicle Inc, Taipei (TW)

(72) Inventors: Dapi Meng Lin Chiang, Taipei (TW); Michael W. Pfaffl, Freising (DE); Dominik Buschmann, Freising (DE)

(73) Assignees: Dapi Meng Lin Chiang, Taipei (TW); Michael W. Pfaffi, Freising (DE); BIOVESICLE INC, Taipei (TW)

( * ) Notice: Subject to any disclaimer, the term of this patent is extended or adjusted under 35 U.S.C. 154(b) by 69 days.

(21) Appl. No.: 16/495,833

(22) PCT Filed: Mar. 20, 2018

(86) PCT No.: PCT/EP2018/057081
§ 371 (c)(1),
(2) Date: Sep. 20, 2019

(87) PCT Pub. No.: WO2018/172384
PCT Pub. Date: Sep. 27, 2018

(65) Prior Publication Data
US 2020/0132682 A1    Apr. 30, 2020

(51) Int. Cl.
G01N 33/553    (2006.01)
G01N 33/543    (2006.01)
G01N 15/14    (2006.01)
G01N 33/53    (2006.01)

(52) U.S. Cl.
CPC ... G01N 33/54326 (2013.01); G01N 15/1404 (2013.01); G01N 33/5306 (2013.01); *G01N 2333/42* (2013.01); *G01N 2333/4724* (2013.01)

(58) Field of Classification Search
CPC ......... G01N 33/54326; G01N 33/5306; G01N 2333/42; G01N 2333/4724; G01N 35/0098; G01N 2400/00
USPC .................. 435/975; 436/526, 806, 808, 827
See application file for complete search history.

(56) References Cited

U.S. PATENT DOCUMENTS

2005/0245737 A1* 11/2005 Cummings .............. C07H 5/06
536/55.3

FOREIGN PATENT DOCUMENTS

WO    WO-2010056337 A2 *    5/2010    ........... G01N 33/574
WO    WO-2013188832 A1 *    12/2013    ............ A61K 35/16

OTHER PUBLICATIONS

Thery et al., Isolation and Characterization of Exosomes from Cell Culture Supernatants and Biological Fluids, Apr. 2006, Current Protocols in Cell Biology, 3.22.1-3.22.29 (Year: 2006).*

(Continued)

*Primary Examiner* — Christopher L Chin (57) ABSTRACT

Disclosed herein are methods and kits for isolating exosomes in a sample. The method comprises contacting and incubating a plurality of galectin-3-modified magnetic beads with the sample, followed by subjecting the mixture to a magnetic field and then isolating the exosomes from the magnetic beads by a lactose solution. The kit of the present disclosure comprises a plurality galectin-3-modified magnetic beads, a lactose solution having a pH value of 6.8 to 7.6, and an exosome-free buffer.

8 Claims, 8 Drawing Sheets

(56) References Cited

OTHER PUBLICATIONS

Idil et al., Concanavalin A immobilized magnetic poly(glycidyl methacrylate) beads for prostate specific antigen binding, Jul. 2015, Colloids and Surfaces B: Biointerfaces, 461-468 (Year: 2015).*

* cited by examiner

| Human Serum | Mice Serum | |
|---|---|---|
| 200 μl | 200 μl | |
|  |  | Alix |
| |  | Rab5 |
|  | | CD63 |
|  |  | CD81 |

METHODS AND KITS FOR EXOSOME ISOLATION AND QUANTIFICATION

TECHNICAL FIELD

The present disclosure relates to methods and kits for isolating and quantifying exosomes in a sample.

BACKGROUND

Exosomes are small vesicles (about 30-150 nm) secreted from different cell types and found in various biological fluids, such as blood, urine, saliva and central spinal fluid (CSF). Exosomes contribute to intercellular signaling, antigen presentation, as well as tumor progression by carrying cellular proteins, RNA/DNA, glycans, and/or lipids. Accordingly, isolation and analysis of exosomes hold the promise of the ability for identification of disease and for insights into the pathological processes involved.

Currently, differential ultracentrifugation (UC) is regarded the 'Gold Standard' for isolating exosomes in a sample. However, UC is a laborious and time-consuming procedure that requires specialized equipment(s) and operational expertise. Several alternative methods such as polyethylene glycol (PEG) or antibody-conjugated beads have been developed to isolate exosomes without UC. Unfortunately, these methods still face different limitations. One major issue for PEG isolation is the purity of the exosome due to PEG remains. Isolation based on antibody-conjugated beads, on the other hand, often involves using an acidic or alkaline reagent to break the antigen-antibody interaction, which may damage the integrity of exosomes.

Moreover, lipoproteins (such as high-density lipoprotein (HDL) and low-density lipoprotein (LDL)) are often co-purified with exosomes because of their floatation density (for HDL) or size (for LDL). For example, Sóclar et al. discloses that current isolation and purification methods for exosomes did not result in lipoprotein-free vesicle preparations from biological fluid samples, and such lipoprotein contamination in the purified exosome preparation may result in overestimate exosome numbers (see, Barbara W Sódar et al., Low-density lipoprotein mimics blood plasma-derived exosomes and microvesicles during isolation and detection, Sci Rep 2016 Apr. 18; 6:24316). Given the fact the lipoproteins are more abundant than exosomes in the biological sample, the lipoprotein contamination in the purified exosome preparation remains challenging.

In view of the foregoing, there exists a need in the art for providing a method for effectively isolating exosomes in a sample without jeopardizing the integrity of the exosomes.

SUMMARY

The following presents a simplified summary of the disclosure in order to provide a basic understanding to the reader. This summary is not an extensive overview of the disclosure and it does not identify key/critical elements of the present invention or delineate the scope of the present invention. Its sole purpose is to present some concepts disclosed herein in a simplified form as a prelude to the more detailed description that is presented later.

The present disclosure relates to methods and kits for use in the isolation and/or quantification of exosomes in a sample. For example, this present disclosure relates to methods and kits for isolating exosomes from uncultured biological samples or cultured samples. In some embodiments, the exosomes are first isolated from the sample in the form of exosome-bead complexes, and these complexes are then eluted with a non-acid and non-alkaline reagent so as to separate the exosomes from the magnetic beads. In this way, the integrity of the isolated exosomes is maintained. According to some other embodiments, the as-isolated exosome-bead complexes are subjected to flow cytometry for quantification of the exosomes.

In one aspect, the present disclosure is directed to a method for isolating and/or quantifying exosomes in a sample. By using a buffer free of exosomes for the isolation of exosomes, the binding efficiency between exosomes and lectin-labelled magnetic beads is substantially increased. As a result, the conventional differentiation ultracentrifugation procedure is avoided. Another beneficial feature of the methods according to some embodiments of the present disclosure is the use of an elution solution of a neutral and physiological pH (about pH 6.8-7.6), which effectively breaks the interaction between the exosome and lectin molecule, and hence maintains the integrity of the exosomes. Moreover, the present method effectively reduces the lipoprotein contamination in the resultant exosome preparation. In view of the foregoing, the present methods provide a facile and efficient way to isolate exosomes from a sample.

According to certain embodiments of the present disclosure, the present method comprises the steps of (a) contacting a plurality of lectin-modified magnetic beads with the sample to obtain a first mixture, wherein the plurality of lectin-modified magnetic beads are suspended in an exosome-free buffer, and each lectin-modified magnetic bead comprises a plurality of lectin molecules that are covalently bonded to the magnetic bead; (b) incubating the first mixture at a condition allowing the exosomes to conjugate with the lectin molecules of the lectin-modified magnetic beads thereby obtaining a second mixture comprising a plurality of exosome-bead complexes; and (c) subjecting the second mixture from the step (b) to a magnetic field, thereby separating the exosome-bead complexes from the remainder of the second mixture.

According to optional embodiments of the present disclosure, the exosome-free buffer is an exosome-free bovine serum albumin or exosome-free human serum albumin.

In optional embodiments of the present disclosure, the method further comprises the step of eluting the exosome-bead complexes from the step (c) using an elution buffer having a pH value of 6.8 to 7.6 so as to separate the exosomes from the magnetic beads. According to some embodiments, the elution buffer comprises a saccharide solution. Non-limiting examples of the saccharide in the saccharide solution include, lactose, lubricin, fetuin, asialofetuin, maltose, arabinose, glucose, galactose, mannose, xylose, fructose, ribose, sucrose, dextran, and dextrin. As an example, rather than a limitation, the saccharide solution is 1-10% (wt %) lactose solution.

In some other embodiments, the present method further comprises the step of quantifying the exosomes by subjecting the exosome-bead complexes from the step (c) to a flow cytometry. For example, the flow cytometry may comprise the step of directly adding a primary antibody to the exosome-bead complexes from the step (c). in optional embodiments, the primary antibody is a conjugated with a fluorescent dye.

In various embodiments, the lectin used in the present method is an animal lectin. Examples of animal lectin include, but are not limited to, galectin-1, -2, -3, -4, -5, -6, -7, -8, -9, -10, -11, -12, -13, -14, and -15. In some embodiments, the lectin is galectin-3.

As could be appreciated, the sample containing exosomes can be an uncultured biological sample obtained from a subject or a cultured sample. For the uncultured biological sample, it may be derived from the peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, pre-ejaculatory fluid, female ejaculate, sweat, fecal matter, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood of the subject. According to certain embodiments of the present disclosure, the subject is a mammalian, such as rodent or human. For example, the sample may be obtained from mice.

In another aspect, the present disclosure is directed to a kit for isolating and/or quantifying exosomes in a sample.

According to some embodiments of the present disclosure, the kit comprises a plurality lectin-modified magnetic beads and an exosome-free buffer. Each of the lectin-modified magnetic beads comprises a plurality of lectin molecules that are covalently bonded to the magnetic bead. The plurality lectin-modified magnetic beads and the exosome-free buffer may be provided in separate containers, or in a single container.

In optional embodiments, the exosome-free buffer is an exosome-free bovine serum albumin or exosome-free human serum albumin.

According to certain embodiments, the kit further comprises an elution buffer having a pH value of 6.8 to 7.6. The elution buffer may be packaged in a separate container. For example, the elution buffer may comprise a saccharide solution. Saccharide solutions discussed above in connection with the above-mentioned aspect of the present disclosure are also applicable herein.

Many of the attendant features and advantages of the present disclosure will becomes better understood with reference to the following detailed description considered in connection with the accompanying drawings.

BRIEF DESCRIPTION OF DRAWINGS

The present description will be better understood from the following detailed description read in light of the accompanying drawings, where.

DESCRIPTION OF EMBODIMENTS

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

For convenience, certain terms employed in the specification, examples and appended claims are collected here. Unless otherwise defined herein, scientific and technical terminologies employed in the present disclosure shall have the meanings that are commonly understood and used by one of ordinary skill in the art.

Unless otherwise required by context, it will be understood that singular terms shall include plural forms of the same and plural terms shall include the singular. Also, as used herein and in the claims, the terms "at least one" and "one or more" have the same meaning and include one, two, three, or more. Furthermore, the phrases "at least one of A, B, and C", "at least one of A, B, or C" and "at least one of A, B and/or C," as use throughout this specification and the appended claims, are intended to cover A alone, B alone, C alone, A and B together, B and C together, A and C together, as well as A, B, and C together.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques. Ranges can be expressed herein as from one endpoint to another endpoint or between two endpoints. All ranges disclosed herein are inclusive of the endpoints, unless specified otherwise.

As used herein, the term "exosome" refers to extracellular vesicles released from cells upon fusion of an intermediate endocytic compartment (the multi-vesicular body (MVB)) with the plasma membrane or those released directly from the plasma membrane. Generally, the diameter of exosomes ranges between 30 to 150 nm.

In this specification, the term "exosome-free buffer" refers to a buffer which is free or essentially free of exosome. By the phrase "essentially free of," it is meant that the amount of the exosome present in the buffer is not detectable using apparatuses or techniques available before the effective filing date of the present application.

Throughout the present application, the term "quantification" or "quantify," or other forms thereof is intended to include both the direct measurement of an analyte (e.g., exosomes) and the relative measurement of the analyte. The direct measurement often involves an exact determination of the absolute amounts of the analytes in the sample. On the other hand, the relative measurement (or semi-quantification) gives approximate amounts of the data.

Many conventional protocols for isolating exosomes involve the use of bovine serum albumin (BSA) or human serum albumin (HSA). The present invention is based, at least, on the fact the presence of minor amount of exosomes in BSA or HSA interferes with the isolation efficiency of exosomes. In view of this, the present disclosure provides a method for isolating and/or quantifying exosomes in a sample by using a buffer that is substantially free of exosomes. Also, a non-antibody coated magnetic bead (EXÖ-Bead) is provided, which, when used with the present exosome-free buffer, potentiates an efficient extraction of exosomes from the sample by forming exosome-bead complexes. Furthermore, instead of using conventional elution buffers that are either acidic or alkaline, the present method uses an elution buffer that has a pH value in the range of the neutral and physiological pH (i.e., about 6.8 to 7.6), which makes possible the release of integral exosomes from the exosome-beads complexes. In view of the foregoing, the present method is able to isolate exosomes in a very elegant and efficient way without differentiation ultracentrifugation. Moreover, due to the increased sensitivity of isolation, exosomes in samples of a minimal volume, e.g., those of less than 10 ml, can be effectively enriched.

In view of the foregoing, the present disclosure provides a method for isolating and/or quantifying exosomes in a sample. As could be appreciated, the sample containing exosomes can be an uncultured biological sample obtained from a subject or a cultured sample. For the uncultured biological sample, it may be derived from the peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, pre-ejaculatory fluid, female ejaculate, sweat, fecal matter, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood of the subject. According to certain embodiments of the present disclosure, the subject is a mammalian, such as rodent or human. For example, the sample may be obtained from mice.

Figure 1:
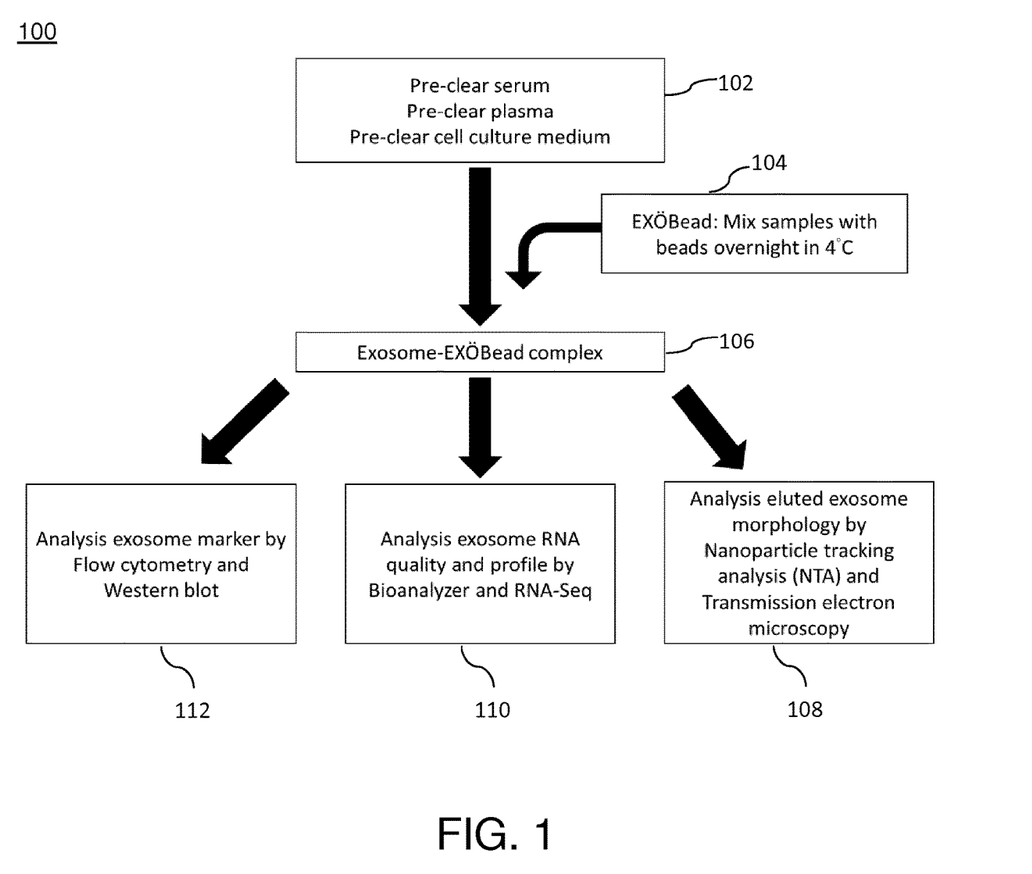
FIG. 1 is a flow diagram illustrating a method according to embodiments of the present disclosure.

According to certain embodiments of the present disclosure, the process steps for carrying out the present method are discussed below in conjunction with FIG. 1, which is a flow diagram illustrating a method 100 for implementing various embodiments of the present disclosure.

According to optional embodiments of the present disclosure, before subjecting a sample to the present method, a pre-clearing step (step 102) is performed to reduce the background. For example, the sample (e.g., serum, plasma, and cell culture samples) may be treated with the conventional pre-clearing reagent or other pre-clearing process. However, as could be appreciated, this pre-clearing step 102 may be skipped in some embodiments of the present disclosure.

The method 100 then proceeds to step 104, in which the sample (pre-cleared or as-obtained) are mixed and incubated with lectin-modified magnetic beads. First, lectin-modified magnetic beads are suspended in an exosome-free buffer; alternatively, an as-provided suspension of lectin-modified magnetic beads in an exosome-free buffer is used. Each of the lectin-modified magnetic beads comprises a plurality of lectin molecules that are covalently bonded to a magnetic bead. According to optional embodiments of the present disclosure, the exosome-free buffer is an exosome-free bovine serum albumin or exosome-free human serum albumin. In various embodiments, the lectin used in the present method is an animal lectin. Examples of animal lectin include, but are not limited to, galectin-1, -2, -3, -4, -5, -6, -7, -8, -9, -10, -11, -12, -13, -14, and -15. In some embodiments, the lectin is galectin-3.

The lectin-modified magnetic beads are then mixed with the sample to give a first mixture. For example, the suspension of lectin-modified magnetic beads is added into the sample.

Next, the first mixture is incubated at a condition that allows the exosomes in the sample to conjugate with the lectin molecules of the lectin-modified magnetic. According to some embodiments, the incubation is carried out at a temperature of 4 to 28° C. for a sufficient time. For example, in some examples, the first mixture is incubated at 4° C. in a rotator overnight, while in some other cases, the first mixture is incubated at the room temperature (about 26 to 28° C.) in a rotator for two hours. In this way, a second mixture that has a plurality of exosome-bead complexes is obtained.

Thereafter, in step 106, the exosome-bead complexes are separated from the remainder of the second mixture. First, the second mixture is placed in a magnetic field under an appropriate condition. For example, in some embodiments, the second mixture is placed on a magnet for 2 minutes, and the supernatant is then removed to give an enriched sample in which the purity (or concentration) of exosomes is substantially increase, as compared with the purity (or concentration) of exosomes in the original sample.

According to optional embodiments, the exosome-bead complexes obtained from the previous step may be resuspended in a washing buffer, which is then subjected to a magnetic field, followed by the removal of supernatant to further increase the purity of the exosomes. This step may be repeated as many times as the operator deems necessary.

In step 108, To further separate the exomes from the exosome-bead complexes, the exosome-bead complexes isolated from the previous step are eluted using an elution buffer. As could be appreciated, it is preferable that the elution buffer used in this step do not comprises an acidic or alkaline reagent that may jeopardize the integrity of the thus-isolated exosomes. Accordingly, the pH value of the elution buffer is in the range of 6.8 to 7.6, which is the neutral physiological pH under the room temperature (about 26 to 28° C.) to the body temperature (about 36 to 38° C.). According to some embodiments, the elution buffer comprises a saccharide solution. Non-limiting examples of the saccharide in the saccharide solution include, lactose, lubricin, fetuin, asialofetuin, maltose, arabinose, glucose, galactose, mannose, xylose, fructose, ribose, sucrose, dextran, and dextrin. In some working examples, the saccharide solution is 1-10% (wt %) lactose solution.

As could be appreciated, in optional embodiments, the eluted exosomes are subject to further analysis (such as nanoparticle tracking andlysis (NTA) or transmission electron microscopy) to examine the morphology of the exosomes thus-obtained.

The method may also proceed to step 110 after step 106, in which the exosomal RNA is analyzed using Bioanalyzer and/or the RNA-Seq technique.

Alternatively, in step 112, to determine the amount of exosomes in the sample, the exosome-bead complexes isolated in the previous step are subject to a flow cytometry. For example, a primary antibody is directly added into the as-isolated exosome-bead complexes. In preferred embodiments, the primary antibody is a conjugated with a fluorescent dye that allows optical determination of the amount of the primary antibody present. As could be appreciated, western blotting may be carried out according to optional embodiments of the present disclosure.

As could be appreciated, a kit for isolating and/or quantifying exosomes in a sample also falls within the scope of the present disclosure.

According to some embodiments of the present disclosure, the kit comprises a plurality lectin-modified magnetic beads and an exosome-free buffer. Each of the lectin-modified magnetic beads comprises a plurality of lectin molecules that are covalently bonded to the magnetic bead. In optional embodiments, the exosome-free buffer is an exosome-free bovine serum albumin or exosome-free human serum albumin. The plurality lectin-modified magnetic beads and the exosome-free buffer may be provided in separate containers, or in a single container.

According to certain embodiments, the kit further comprises an elution buffer having a pH value of 6.8 to 7.6. The elution buffer may be packaged in a separate container. For example, the elution buffer may comprise a saccharide solution. Saccharide solutions discussed above in connection with the above-mentioned aspect of the present disclosure are also applicable herein.

The following Examples are provided to elucidate certain aspects of the present invention and to aid those of skilled in the art in practicing this invention. These Examples are in no way to be considered to limit the scope of the invention in any manner. Without further elaboration, it is believed that one skilled in the art can, based on the description herein, utilize the present invention to its fullest extent.

EXAMPLE 1

Preparation of Lectin-Modified Magnetic Beads

In an Eppendorf tube (1.5 mL), 20 mg of carboxyl group magnetic latex beads (from IKERLAT polymers) was added. To replace the original magnetic bead buffer with 1 mL 2-(N-morpholino)ethanesulfonic acid (MES; Sigma-Aldrich) buffer (pH 5.0), the tube was placed on a magnet for 2 minutes, and after the supernatant was removed, the pellet was resuspended with 1 mL MES buffer by thoroughly pipetting. After removing the supernatant, 0.25 mL MES buffer containing 10 mg 1-Ethyl-3-(3-dimethylaminopropyl)-carbodiimide (EDC; ThermoFisher) was added into the tube and then mixed on a shaker for 10 minutes at the room temperature. The beads were washed with 1 mL MES buffer twice, and then the activated beads were resuspended in 0.25 mL MES buffer. Thereafter, 50 µg galectin-3 protein (R&D Systems) dissolved in ddH$_2$O was added, and the reaction mixture was mixed using a shaker for one hour at the room temperature and additional 15 minutes at 37° C. The magnetic beads were then washed twice using 1 mL of EXÖ-Beads buffer (1% exosome-free BSA in phosphate-buffered saline (PBS) (10% BSA in PBS, 100,000 G ultracentrifugation for 16 hours). The beads (hereinafter, EXÖBeads) were resuspended in 1 mL EXÖBeads buffer and stored for subsequent use.

EXAMPLE 2

Isolation of Exosome-Bead Complexes from the Sample

Human THP-1 macrophage cells were cultured in 10% exosome-free fetal bovine serum (FBS) DMEM medium. Human serum sample was collected from volunteers with informed consent. Mice serum sample was obtained from C57BL/6 mice per general protocols.

Pre-cleared biological samples were prepared as follows. (1) The cell culture or serum sample was first centrifuged with 350 g at 4° C. for 10 minutes, and the pellet was discarded to remove dead cells. (2) The supernatant was then centrifuged with 2,000 g at 4° C. for 15 minutes, and the pellet was discarded to remove dead cell debris. For the cell culture sample, the supernatant from the step (2) was then passed through a 0.22 µm filter (Millipore), and the filtrate was collected and used as the pre-cleared biological sample. For the serum sample, the supernatant from the step (2) was then centrifuged with 10,000 g at 4° C. for 30 minutes, and the resultant supernatant was used as the pre-cleared biological sample.

100 µL of EXÖBeads from Example 1 were added into the pre-cleared biological sample (10 mL), and incubated at 4° C. overnight in a rotator. The reaction mixture was then washed twice with 1 mL of EXÖBeads washing buffer, and the supernatant was removed by placing the tube on a magnet for 2 minutes.

The resultant exosome-bead complexes were examined under transmission electron microscopy (TEM). Briefly, the exosome-bead complexes were fixed by 2% paraformaldehyde fixation buffer and placed directly on Formvar/Carbon-coated TEM grid (Electron Microscopy Sciences) at room temperature (RT) for 15 minutes. Next, the exosome-bead complexes were washed thrice with 200 µl of PBS droplets on parafilm. The exosome-bead complexes were then fixed by 2.5% glutaraldehyde fixation buffer at RT 15 for minutes. After the fixation, the exosome-bead complexes were washed thrice with 200 µl of DI water droplets on parafilm. Thereafter, the exosome-bead complexes were stained with 0.5% Uranyl acetate in DI water at RT for 15 minutes. The exosome-bead complexes were washed five times with 200 µl of DI wate The specimen was analyzed with electron microscope (JEOL JEM-2100F) equipped with a CCD camera (Gatan UltraScan 1000 (2k×2k) CCD camera).

Figure 2:
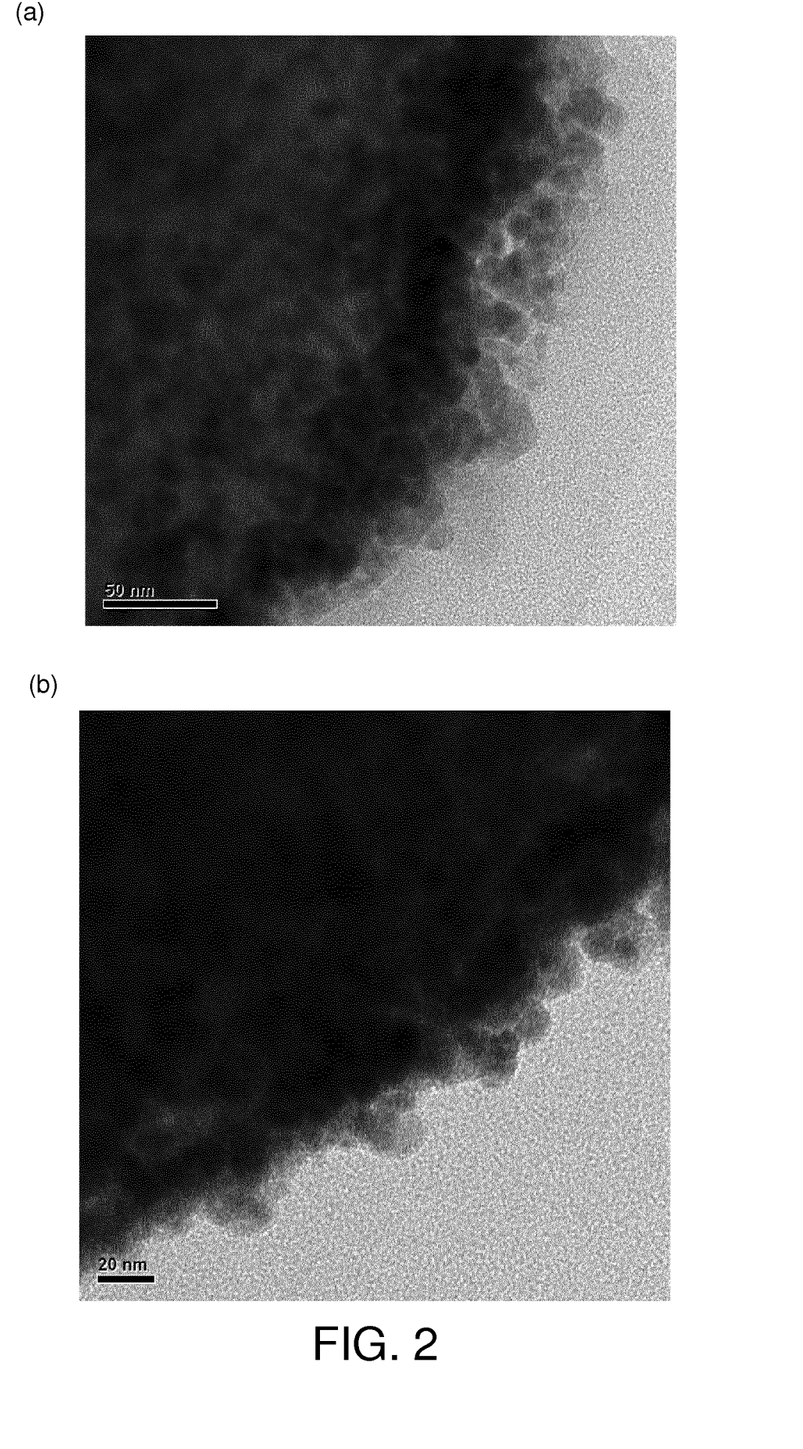
FIG. 2 provides representative TEM photographs of the exosome-bead complexes prepared from human serum sample according to one working example of the present disclosure.

FIG. 2 provides two representative TEM photographs of the exosome-bead complexes prepared from 200 µl human serum sample. As could be seen in panels (a) and (b) of FIG. 2, there were many exosomes (indicated with arrowheads) conjugated to one EXÖBead; also, some exosomes were aggregated into exosome clusters.

EXAMPLE 3

Analysis of Exosome-Bead Complexes

In this example, the pulled-down fractions from Example 2 were analyzed by fluorescence-activated cell sorting (FACS), western blot, and bioanalyzer.

(1) FACS analysis

In this analysis, exosomes were detected using well-known exosomal markers, CD63 and CD81. For FACS analysis, 200 µL of 2.5 µg/mL mouse anti-human CD63 antibody and FITC-goat anti-mouse IgG (for human THP-1 macrophage cells), mouse anti-human CD63 antibody or Alexa Fluor 647-donkey anti-mouse IgG (for human serum sample) was directly added into the exosome-bead complexes; the samples were immune labeled at 4° C. overnight. After staining, the unbound antibodies were removed by washing with 1 mL EXÖbuffer. The antibody-stained exosome-beads complexes were analyzed using BD Biosciences FACSCanto II (BD Biosciences), and the flow cytometry data were analyzed with FlowJo software (Tree Star, Ashland, Oreg.).

Figure 3:
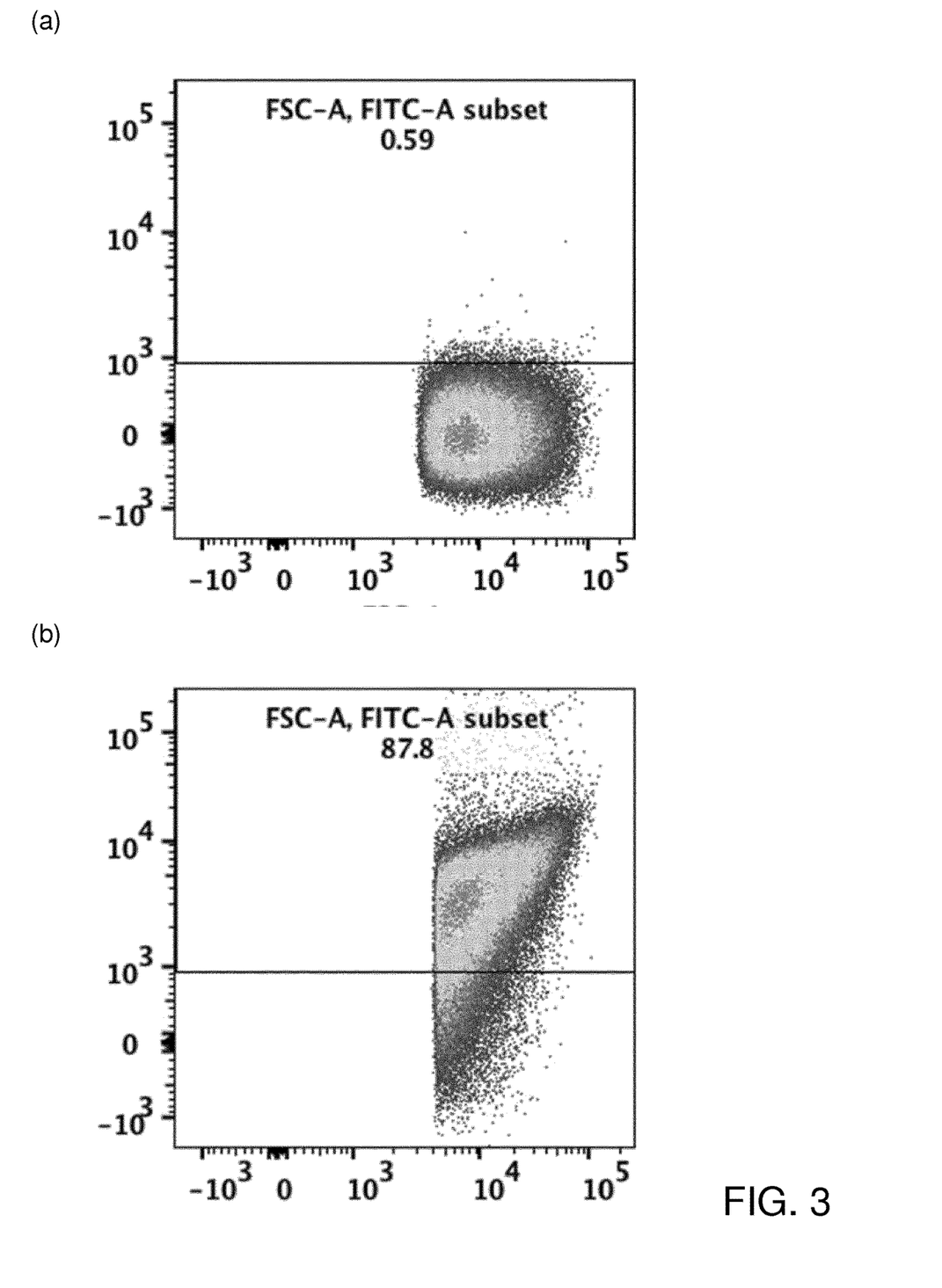
FIG. 3 provides representative flow cytometry (FCM) plot diagrams of mice cell culture supernatants according to one working example of the present disclosure.

FIG. 3 provides representative flow cytometry (FCM) plot diagrams. In the FCM plots, the y-axis represents the median Fluorescence Intensity (MFI), while the x-axis represents forward scatter (FSC). The FACS analysis results indicated that in the exosome-free medium control, only a few non-specific antibody binding signals (0.59% CD63 positive population, median fluorescence intensity: 1.28) within the size range of beads were recognized by the CD63 antibody (panel (a), FIG. 3). On the other hand, as the volume of human THP-1 macrophage cells medium used for preparing the sample increased, the number of CD63-positive events in said size range increased significantly to 87.8% with a median fluorescence intensity of 3,004 (10 mL; panel (b), FIG. 3).

Figure 4:
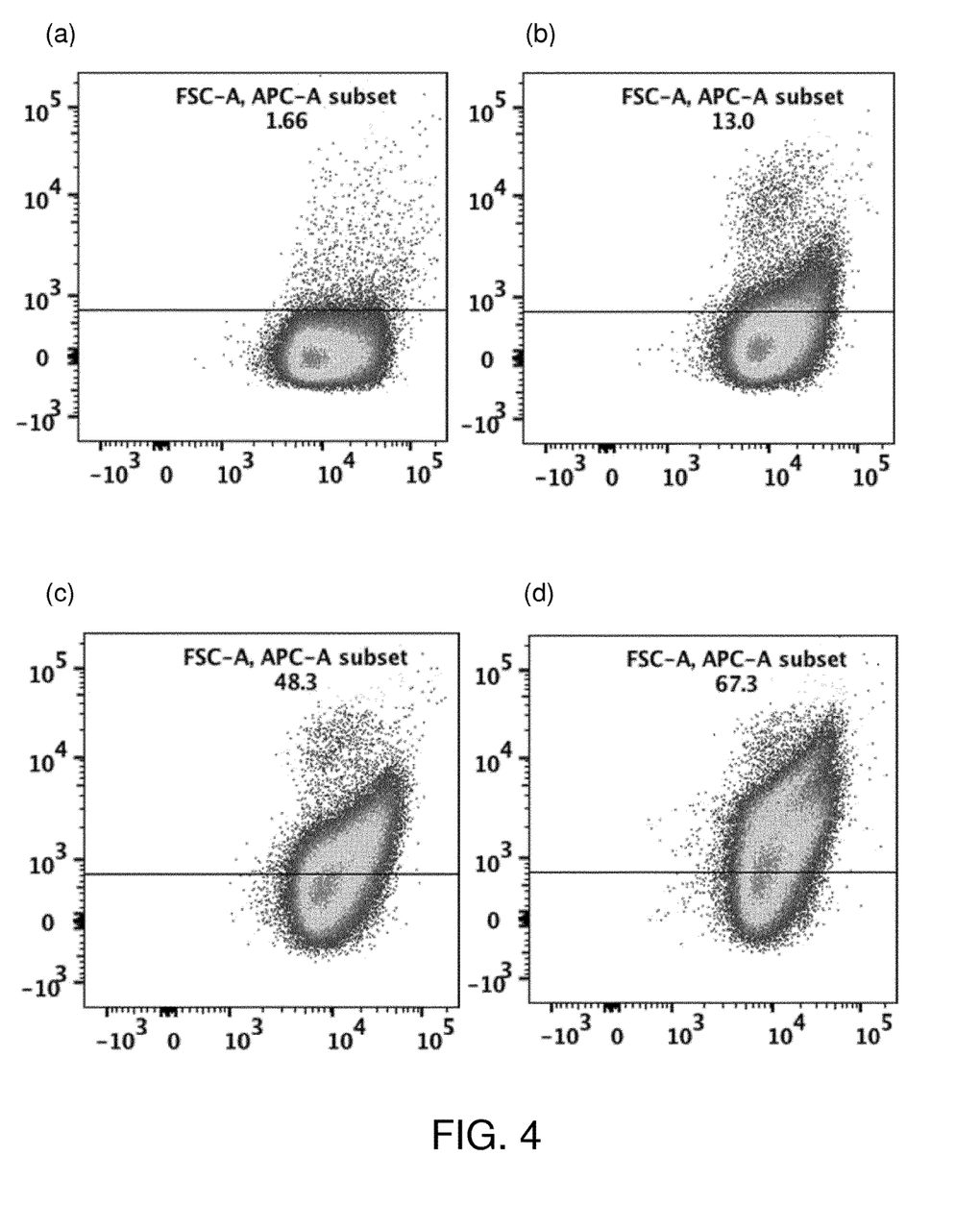
FIG. 4 includes representative plot diagrams of human serum samples according to one working example of the present disclosure.

FIG. 4 includes representative plot diagrams of human serum samples. The data in FIG. 4 indicated that in samples without human serum and with exosome-free 10% FBS RPMI medium (negative control), CD63-positive events in the size range of interest was about 1.66% with a median fluorescence intensity of 37.2 (panel (a), FIG. 4). In contrast, when the samples containing 250 µL (panel (b), FIG. 4) human serum from a first donor were used, the detected CD63-positive events in the specified size range accounted for about 13.0%, and the median fluorescence intensity was 259. Moreover, the serum samples from a for second donor and third donor, the CD63-positive events in the size range of interest was about 48.3% with a median fluorescence intensity: 722 (panel (c), FIG. 4), and 67.3% with median fluorescence intensity: 1156 (panel (d), FIG. 4), respectively.

(2) Western Blotting Analysis: exosome-beads complexes were directly loaded into SDS-PAGE, and the gel was run for at least 30 minutes at a low voltage of 50 to 70 V (dye through the upper gel); the voltage was then raised to a high voltage of 100 to 110 V (running time dependent on the protein molecular weight). Thereafter, the gel was transferred in a "4° C. Cold room" at 280 mA for 90 minutes (also 30V for overnight in cold room), membranes were blocked with 5 (w/v) BSA in PBS for 1 hour at RT, and then incubated with the primary antibody (dilution ratio: 1:500 to 1:1000) at 4° C. overnight. The membranes were washed with 0.1% Tween-20 in PBS three times, and then incubated with the secondary antibody (dilution ratio: 1:2000 at least) at 4° C. overnight. Next, the membranes were washed with 0.1% Tween-20 in PBS three times for 10 minutes at room temperature and applied to the chemiluminescent substrate.

Figure 5:
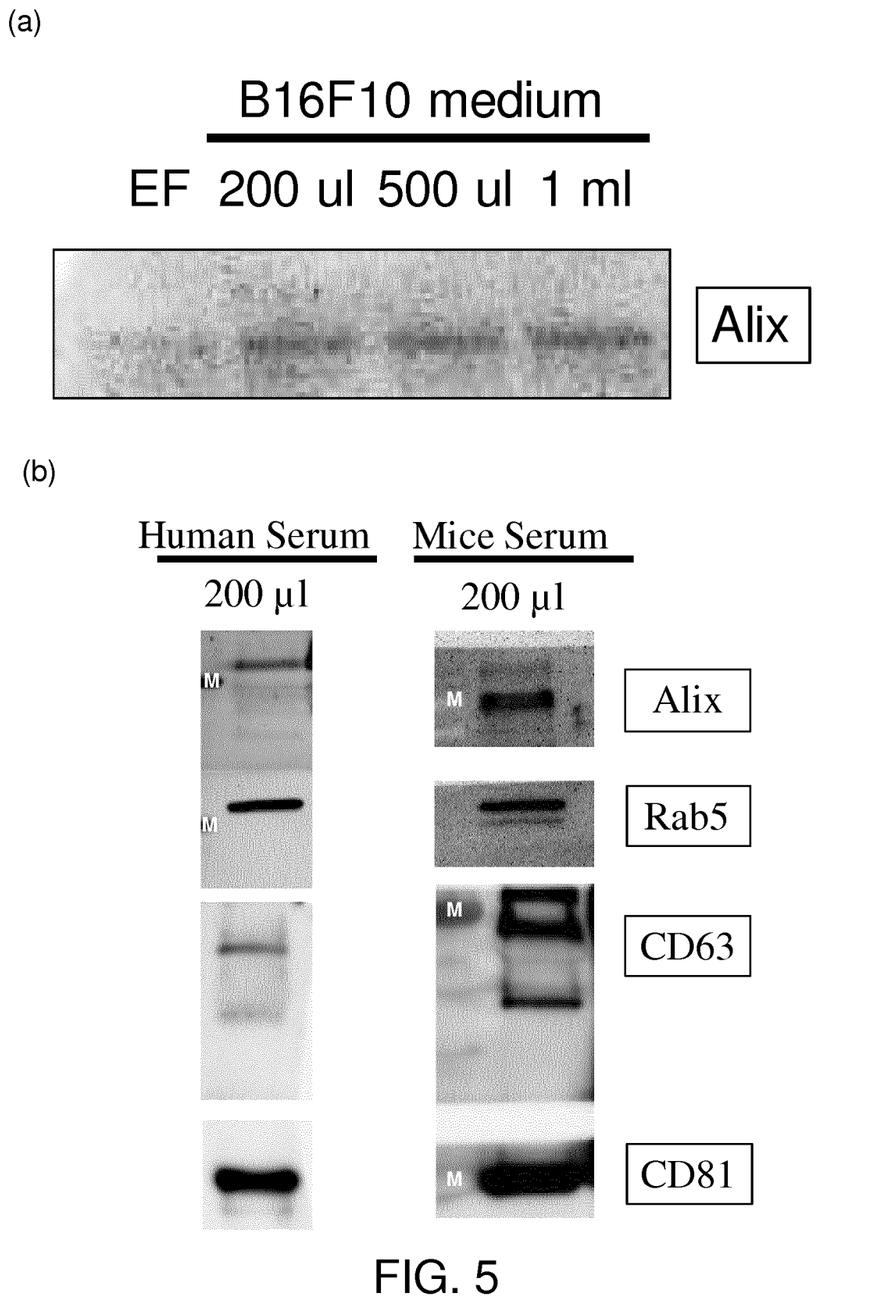
FIG. 5 provides Western blot photographs according to of one working example of the present disclosure.
Figure 6:
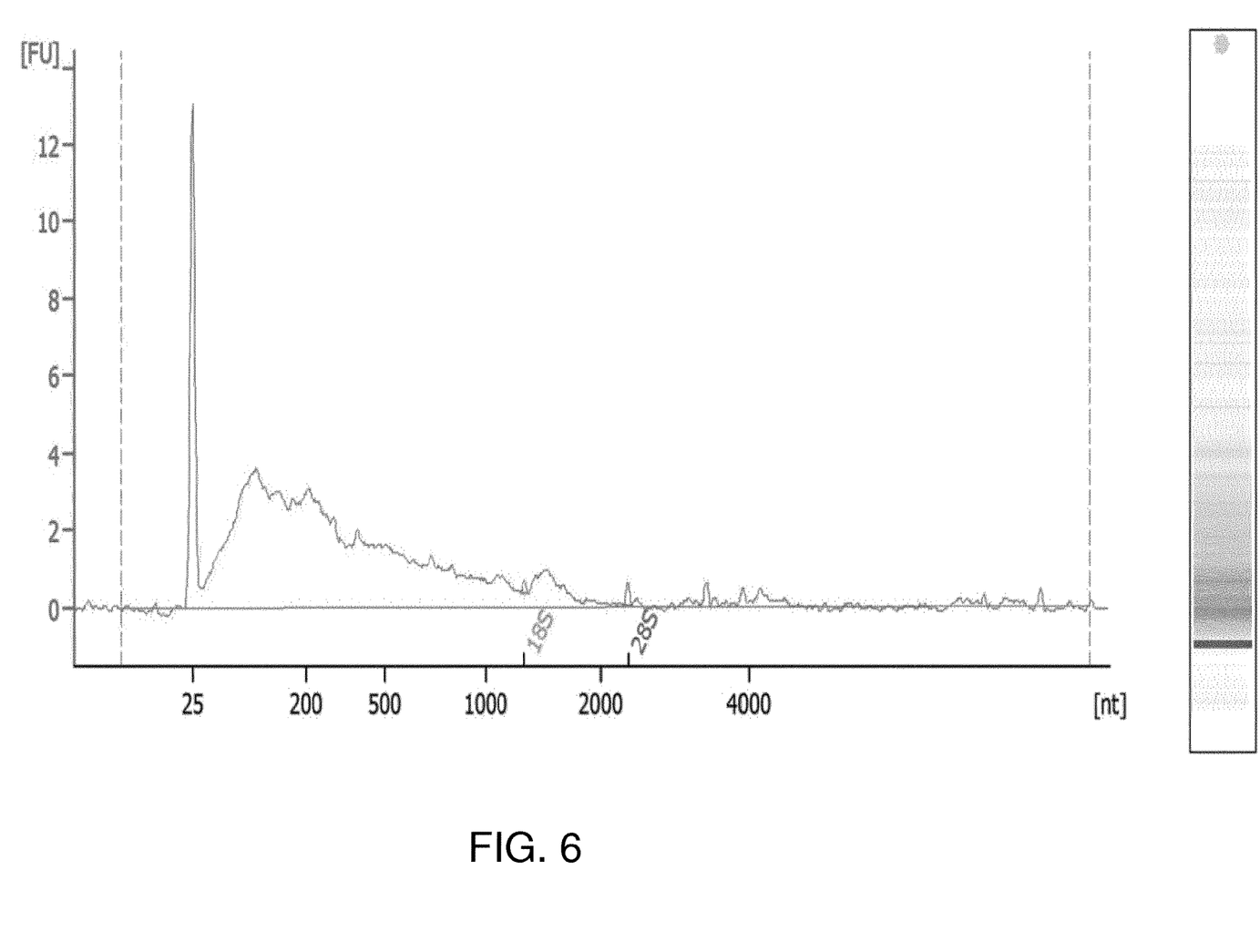
FIG. 6 is the cDNA profile of microRNAs from samples according to of one working example of the present disclosure.

The expression of Alix and Rab5 was substantiated by western blot using the exosome-EXÖBead complex prepared from 0.2 to 1 mL of B16F10 control-conditioned medium (CCM) (panel (a), FIG. 5) and 200 µL of mouse serum (panel (b), FIG. 5)

RNA Analysis

For RNA analysis, EVs were isolated from 1.5 ml of serum from a healthy volunteers using EXÖBead. RNA was extracted from EXÖBead-captured EVs using the miRNeasy Mini Kit (Qiagen) per the manufacturer's instructions. The total RNA including miRNA was eluted in 50 µL of nuclease-free water. Length profiles of eluted RNA were assessed using capillary electrophoresis (Agilent 2100 Bioanalyzer, RNA Pico Assay). RNA isolated by EXÖBead featured a prominent peak at approximately 25-100 nucleotides.

EXAMPLE 4

Isolation of Exosomes from Exosome-Bead Complexes

The exosome-bead complexes from mice serum as prepared in Example 2 were eluted with the EXÖBead elution buffer (10% lactose in EXÖBeads buffer) to separate exosomes from the exosome-bead complexes. Briefly, exosome-EXÖBead complex homogeneously incubate with 200 µL EXÖBead elution buffer by pipetting and mixing at room temperature for 1 hour.

EXAMPLE 5

Analysis of Eluted Exosomes (1) Nanoparticle Tracking Analysis

Figure 7:
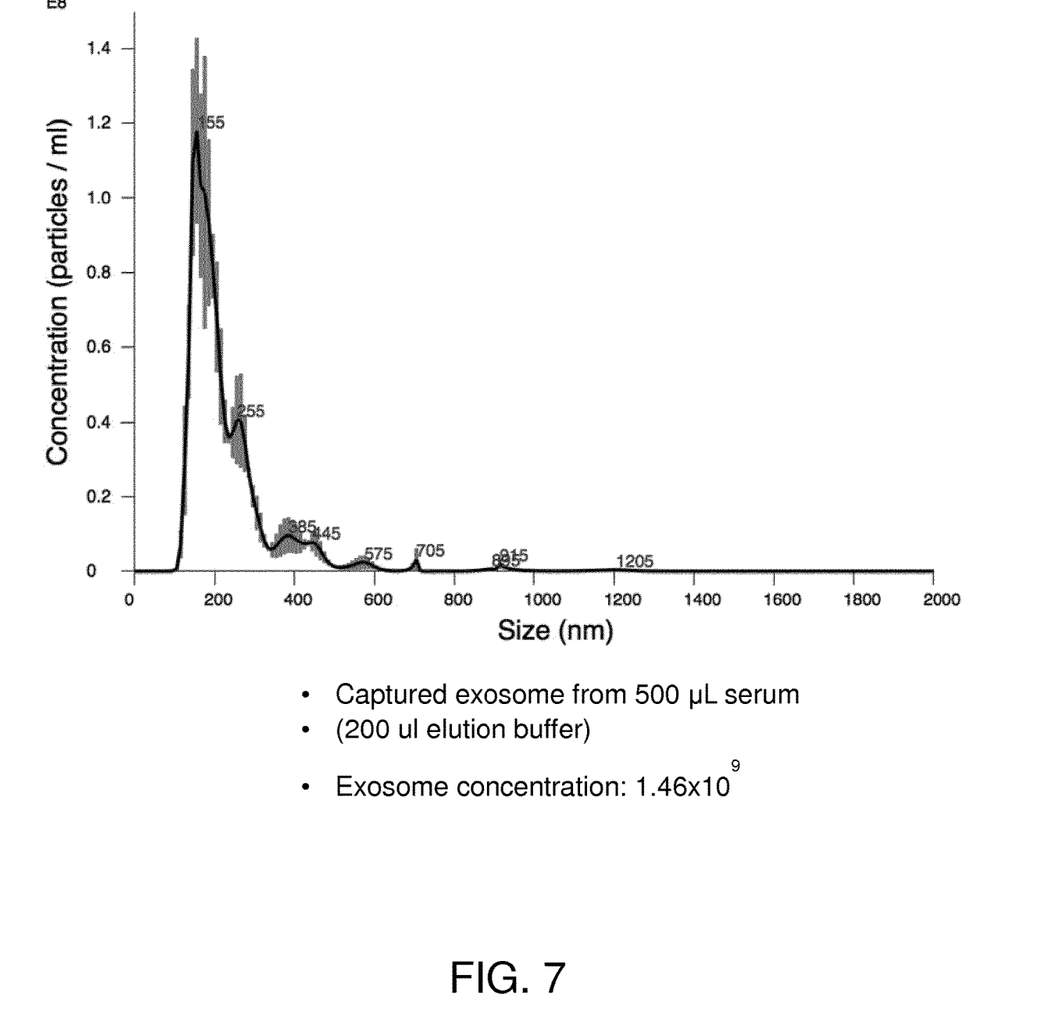
FIG. 7 illustrates the size distribution of eluted exosomes according to of one working example of the present disclosure.

To investigate the ability of the present EXÖBead elution buffer to release exosomes from the beads, nanoparticle tracking analysis (NTA) was performed to measure exosome size and its distribution. FIG. 7 illustrates the size distribution of the exosomes eluted from samples containing 500 µL mice serum. The size of exosomes eluted from beads was quite similar to exosomes isolated by conventional differential ultracentrifugation (data not shown).

(2) TEM Analysis

Figure 8:
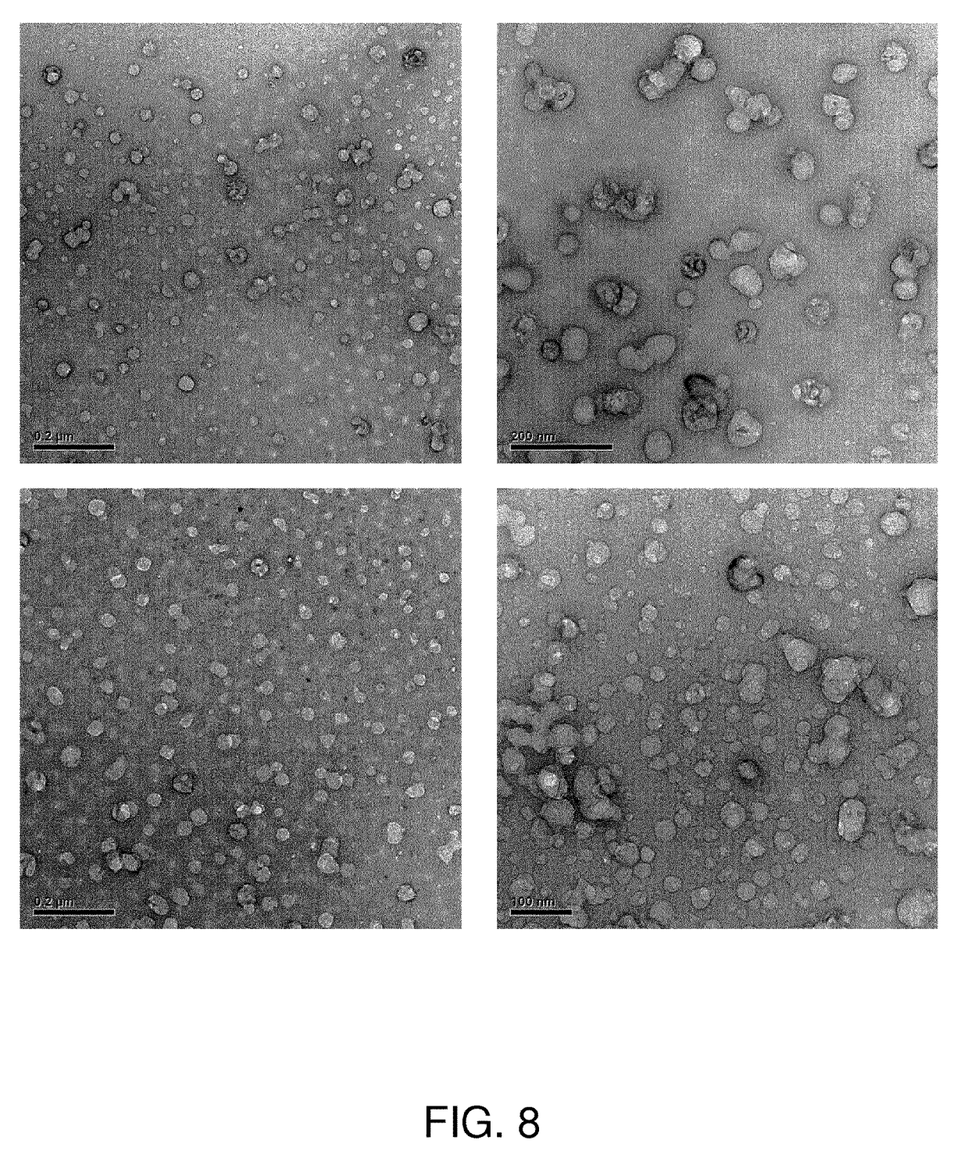
FIG. 8 provides representative TEM photographs of eluted exosomes according to of one working example of the present disclosure.

TEM specimens were prepared as discussed above in Example 2. As could be appreciated, lipoprotein particles are electron dense, and accordingly, they can be identified as dark structures in TEM photographs. Referring to FIG. 8, which presents four representative TEM photographs in indicated that the exosomes eluted by the present method. As could be seen in FIG. 8, the eluted exosomes maintained good integrity. Also, only a minimal amount of lipoproteins was observed in the TEM photographs. In view of the foregoing, the present isolation method effectively reduces the lipoprotein contamination encountered in the prior art.

In conclusion, the present method and the EXÖBead kit provide an easy, fast and reproducible isolation method for researcher working with small amounts of starting material.

It will be understood that the above description of embodiments is given by way of example only and that various modifications may be made by those with ordinary skill in the art. The above specification, examples, and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A method for isolating exosomes in a sample, comprising the steps of,
   (a) contacting a plurality of lectin-modified magnetic beads with the sample to obtain a first mixture, wherein the plurality of lectin-modified magnetic beads are suspended in an exosome-free buffer, and each lectin-modified magnetic bead comprises a plurality of lectin molecules that are covalently bonded to the magnetic bead, wherein the exosome-free buffer is an exosome-free bovine serum albumin or exosome-free human serum albumin, and the lectin is galectin-3;

(b) incubating the first mixture at a condition allowing the exosomes to conjugate with the lectin molecules of the lectin-modified magnetic beads thereby obtaining a second mixture comprising a plurality of exosome-bead complexes;

(c) subjecting the second mixture from the step (b) to a magnetic field, thereby separating the exosome-bead complexes from the remainder of the second mixture; and (d) separating the exosomes from the magnetic beads by eluting the exosome-bead complexes from the step (c) using an elution buffer having a pH value of 6.8 to 7.6, wherein the elution buffer is a lactose solution consisting essentially of lactose.

2. The method according to the claim 1, wherein the lactose solution is 1-10% (wt %) lactose solution.

3. The method according to claim 1, wherein the sample is an uncultured biological sample obtained from a subject.

4. The method according to the claim 3, wherein the uncultured biological sample is derived from peripheral blood, serum, plasma, ascites, urine, cerebrospinal fluid (CSF), sputum, saliva, bone marrow, synovial fluid, aqueous humor, amniotic fluid, cerumen, breast milk, broncheoalveolar lavage fluid, semen, prostatic fluid, pre-ejaculatory fluid, female ejaculate, sweat, fecal matter, tears, cyst fluid, pleural and peritoneal fluid, pericardial fluid, lymph, chyme, chyle, bile, interstitial fluid, menses, pus, sebum, vomit, vaginal secretions, mucosal secretion, stool water, pancreatic juice, lavage fluids from sinus cavities, bronchopulmonary aspirates, blastocyl cavity fluid, or umbilical cord blood of the subject.

5. The method according to claims 3, wherein the subject is a human.

6. The method according to claim 1, wherein the sample is a cultured sample.

7. A kit for isolating and exosomes in a sample, comprising, a plurality of lectin-modified magnetic beads, an elution buffer having a pH value of 6.8 to 7.6, and an exosome-free buffer, wherein each lectin-modified magnetic bead comprises a plurality of lectin molecules that are covalently bonded to the magnetic bead, wherein the lectin is galectin-3;

the elution buffer is a lactose solution consisting essentially of lactose; and the exosome-free buffer is an exosome-free bovine serum albumin or exosome-free human serum albumin.

8. The kit according to the claim 7, wherein the lactose solution is 1-10% (wt %) lactose solution.

* * * * *